United States Patent [19]
Marrone et al.

[11] Patent Number: 6,004,774
[45] Date of Patent: Dec. 21, 1999

[54] BIOLOGICAL CONTROL OF PLANT FUNGAL INFECTIONS

[75] Inventors: Pamela Gail Marrone; Sherry D. Heins; Denise C. Manker, all of Davis; Desmond R. Jimenez, Woodland, all of Calif.; Richard K. Bestwick, Portland, Oreg.; George J. Vandemark, Prosser, Wash.

[73] Assignee: Agritope, Inc., Portland, Oreg.

[21] Appl. No.: 09/199,871

[22] Filed: Nov. 25, 1998

Related U.S. Application Data

[63] Continuation of application No. PCT/US97/21149, Nov. 18, 1997, and a continuation-in-part of application No. 08/746,893, Nov. 18, 1996, Pat. No. 5,753,222.

[51] Int. Cl.$^6$ .............................. C12N 1/20; C12N 1/00; A01N 63/00
[52] U.S. Cl. .................. 435/41; 424/93.462; 424/93.46; 424/115; 424/123; 424/404; 424/405; 435/71.1; 435/71.2; 435/71.3; 435/252.31; 435/839
[58] Field of Search .......................... 435/41, 71.1, 71.2, 435/71.3, 252.31, 839; 424/93.462, 93.46, 115, 123, 404, 405

[56] References Cited

U.S. PATENT DOCUMENTS

| | | |
|---|---|---|
| 4,582,704 | 4/1986 | Baker . |
| 4,764,371 | 8/1988 | Pusey et al. ........................ 424/93.462 |
| 5,047,239 | 9/1991 | Pusey . |
| 5,049,379 | 9/1991 | Handelsman et al. . |

FOREIGN PATENT DOCUMENTS

| | | |
|---|---|---|
| 02 209803 | 8/1990 | Japan . |
| 06 133 763 | 5/1994 | Japan . |
| 1 738 200 | 6/1992 | U.S.S.R. . |
| WO 94/09630 | 5/1994 | WIPO . |

OTHER PUBLICATIONS

Asante et al., "Characterization of fungistatic substances produced by a bacillus antagonistic to ceratocystis ulmi" *Phytopathol.* (1964) 54:819–822.
Babad et al., "An antifungal polypeptide produced by *Bacillus subtilis*" *Nature* (1952) 170:618–619.
Baker et al., "Inhibitory effect of *Bacillus subtilis* on *Uromyces phaseoli* and on development of rust pustules on bean leaves" *Phytopathol.* (1983) 73:1148–1152.
Burachik et al., "Three antifungal polypeptides from *Bacillus subtilis*" *Experientia* (1964) 20:504–505.
Campbell, Biological Control of Microbial Plant Pathogens. Cambridge University Press. A title page and table of contents are included herewith.
Ferreira et al., "Biological control of *Eutypa lata* on grapevine by an antagonistic strain of *Bacillus subtilis*" *Phytopathol.* (1991) 81:283–287.
Gueldner, R.C. et al., "Isolation and Identification of Iturins as Antifungal Peptides in Biological Control of Peach Brown Rot with *Bacillus subtilis,*" *J. Agric. Food Chem.* (1988) 36:366–370.

Handelsman et al., "Biological control of damping–off of alfalfa seedings with *Bacillus cereus* UW 85" *Appl. Environ. Microbiol.* (1990) 56:713–718.
He et al, "Zwittermicin A, an antifungal and plant protection agent from *Bacillus cereus*" *Tetra. Lett.* (1994) 35:2499–2502.
Johnson et al., "Eumycin–a new antibiotic active against pathogenic fungi and higher bacteria, including bacilli of tuberculosis and diptheria" *J. Bacteriol.* (1946) 51:591.
Landy et al., "Bacillomycin: An antibiotic from *Bacillus subtilis* active against pathogenic fungi" *Proc. Soc. Exp. Bio Med.* (1948) 67: 539–541.
Leifert et al., "Antibiotic production and biocontrol activity by *Bacillus subtilis* CL27 and *Bacillus pumilus* CL45" *J. Appl Bacteriol.* (1995) 78–97–108.
McKeen et al., "Production and partial characterization of antifungal substances antagonistic to *Monilinia fructicola* from *Bacilus subtilis*" *Phytopathol.* (1986) 76:136–139.
Michener et al., "Two antifungal substances from *Bacilus subtilis* cultures" *Arch. Biochem.* (1959) 22:208–214.
Milner et al., "Production of Kanosamine by *Bacillus cereus* UW85" *Appl. Environ. Microbiol.* (1996) 62:3061–3065.
Osburn et al., "Effect of *Bacillus cereus* UW85 on the yield of soybean at two field sites in Wisconsin" *Am. Phytophataol. Soc.* (1995) 79:551–556.
PCT International Search Report for PCT/US97/21149 dated Apr. 21, 1998.
Pusey et al., "Pilot tests for commercial production and application for *Bacillus subtilis* (B–3) for postharvest control of peach brown rot" *Plant Disease* (1988) 72:622–626.
Rodgers, "Potential of biopesticides in agriculture" *Pestic Sci* (1993) 39:117–129.
Schwinn et al., "Control with Chemicals" Advances in Plant Pathology: vol. 7: *Phytophtohora infestans*, the Cause of Late Blight of Potato, Ingram et al., eds., Academic Press, San Diego. (1991) 8:255–266.
Sholberg et al., "Biocontrol of postharvest diseases of apple using Bacillus spp. isolated from stored apples" *Can J. Microbiol.* (1995) 41:247–252.
Silo–Suh et al., "Biological activities of two fungistatic antibiotics produced by *Bacillus cereus* UW85" *Appl. Environ. Microbiol.* (1994) 60: 2023–2030.
Singh et al., "*Bacillus subtilis* as a control agent against fungal pathogens of citrus fruit" *Trans. Br. mycol. Soc.* (1984) 83:487–490.
Smith et al., "Suppression of cottony leak of cucumber with *Bacillus Cereus* strain UW85" *Plant Disease* (1993) 77:139–142.
Stabb et al., "Zwittermicin A –producing strains of *Bacillus cereus* from diverse soils" *Appl. Environ. Microbiol.* (1994) 60:4404–4412.
Swinburne et al., "Production of antibiotics by *Bacillus subtilis* and their effect on fungal colonists of apple leaf scars" *Trans. Br. mycol. Soc.* (1975) 65:211–217.
*Westcott's Plant Disease Handbook*, 4$^{th}$ ed., Revised by R. Kenneth Horst, PhD., (1979) pp. 110–113; 138–143.

*Primary Examiner*—Herbert J. Lilling
*Attorney, Agent, or Firm*—Antoinette F. Konski

[57] ABSTRACT

The present invention is directed to a unique strain of *Bacillus subtilis* for inhibiting growth of plant pathogenic fungi and bacteria and methods for treating or protecting plants from fingal and bacterial infections.

4 Claims, 5 Drawing Sheets

BIOLOGICAL CONTROL OF PLANT FUNGAL INFECTIONS

This application is a continuation of International Application No. PCT/US97/21149, filed on Nov. 18 1997, designating the United States, and a continuation-in-part of U.S. patent application Ser. No. 08/746,893, filed on Nov. 18 1996, now U.S. Pat. No. 5,753,222, which are hereby incorporated by reference.

FIELD OF THE INVENTION

The present invention relates to a strain of *B. subtilis* for inhibiting growth of plant pathogenic fungi, and to methods for protecting a plant against fingal and bacterial infections.

REFERENCES

1993 PACIFIC NORTHWEST PLANT DISEASE CONTROL HANDBOOK Oregon State Dept. of Agricultural Extension (1993).

Agrios, G. N., PLANT PATHOLOGY, 3rd Edition, Academic Press, Inc.. New York, pp. 403–408 (1988).

Assante and Neal, *Phytopathol.* 54:819–822.

ATCC MEDIA HANDBOOK, 1st Edition, American Type Culture Collection, Rockville, Md, pp. 17 (1984).

Bahad et al., *Nature* 170:618–619 (1952).

Baker et al., *Phytopathol.* 73:1148–1152 (1983).

Baker and Stavely, U.S. Pat. No. 4,582,704.

Burachik et al., *Experientia* 20:504–505 (1964).

English, J. T., et al., *Phytopathol.* 79:395–401 (1989).

Ferreira et al., *Phytopathol.* 81:283–287 (1991).

Gross, D. C., arid DeVay, J. E., *Physiolog. Plant Pathol.* 11:13–28 (1977).

Gross, D. C., eta., *J. App. Bacteriol.* 43:453–463 (1977).

Gubler, W. D., et al., *Plant Disease* 71:599–601 (1987).

Handelsman et al., U.S. Pat. No. 5,049,379.

He et al., *Tetra. Lett.* 35(16):2499–2502 (1994)

Johnson and Burdon, *J. Bacteriol.* 51:591 (1946).

Landy et al., *Proc. Soc. Exp. Biol. Med.* 67:539–541 (1948).

Leifert, C., et al., *Plant Pathology* 42:270–279 (1993).

Leifert et al., *J. Appl. Bacteriol.* 78:97–108 (1995).

McKeen et al., *Phytopathol.* 76:136–139 (1986).

Michener and Snell, Arch. Biochem. 22:208–214 (1959).

Milner et al., *Appl. Environ. Microbiol.* 62:3061–3065 (1996).

Osburne et al., *Am. Phytopathol. Soc.* 79(6):551–556 (1995).

Pscheidt, J. W., *Fungicide and Nematicide Tests* 46(91) :#90 (1990).

Pscheidt, J. W., *Fungicide and Nematicide Tests* 47(66) :#63 (1991).

Pusey et al., *Plant Dis.* 72:622–626 (1988).

Pusey and Robins, U.S. Pat. No. 5,047,239.

Rossall, U.S. Pat. No. 5,061,495.

Schaad, N. W., Ed., LABORATORY GUIDE FOR IDENTIFICATION OF PLANT PATHOGENIC BACTERIA, 2nd Ed., APS Press, Minneapolis, Minn., pp. 23, 60–80 (1988).

Schroth, M. N., et al., in SELECTIONS FROM THE PROKARYOTES, A HANDBOOK ON HABITATS, ISOLATION AND IDENTIFICATION OF BACTERIA, (Starr, M. P., Ed.) Springer-Veriag, New York, N.Y., Chapter 60 (1983).

Schwinn et al., p. 244, in ADVANCES IN PLANT PATHOLOGY: PHYTOPHTHORA INFESTANS, THE CAUSE OF LATE BLIGHT POTATO, Academic Press, San Diego (1991).

Sholberg et al., *Can. J. Microbiol.* 41:247–252 (1995).

Singh and Deverall, *Trans. Brit. Mycol. Soc.* 83:487–490 (1984).

Smith et al., *Plant Disease* 77(2):139–142 (1993).

Stabb et al., *App. Environ. Microbiol.* 60(12):4404–4412.

Swinburne et al, *Trans. Brit. Mycol. Soc.* 65:211–217 (1975).

Weller, D. M., *Annual Review of Phytopathology* 26:379–407 (1988).

Wollum, A. G., "Cultural Methods for Soil Microorganisms," in METHODS OF SOIL ANALYSIS PART 2, Second Edition, American Society of Agronomy/Soil Science Society of America, Madison, Wis., pp. 785 (1982).

BACKGROUND OF THE INVENTION

Microbial infection of plants, meaning infection due to a fungal, bacterial or viral agent, is a significant agricultural problem, often resulting in pronounced loss of crop quality and useability.

Plants are susceptible to attack by a variety of phytopathogenic fimgi. One particularly damaging plant phytopathogenic fungus is *Botrytis cinerea* Pers, and plant diseases caused by Botrytis sp. are some of the most widely distributed and common diseases of greenhouse-grown crops, field crops, vegetables, ornamentals, and fruits throughout the world. One species of Botrytis, *B. cinerea*, is the causal agent of several severe fruit diseases, including grey mold of strawberry (*Fragaria ' ananassa Duchesne*) and grapevine (*Vitis vinifera L.*) (Agrios, 1988). Botrytis-related diseases cause losses not only in the field, but also in storage, in transit, and in the targeted wholesale and retail markets.

Other detrimental fungal plant pathogens include *Fusarium oxysporum*, which causes wilt in numerous plants, *Sclerotinia sclerotiorum*, which causes scelerotinia wilt, and *Rhizoctonia solani*, which can cause seedling damping off and root rot disease. Additional genera of phytopathogenic fungi include Aspergillus, Penicillium, Ustilago, and Tilletia.

The control of phytopathogenic fungi is of significant economic importance, since fungal growth on plants or parts of plants (e.g., seeds, fruits, blossoms, foliage, stems, tubers, roots, etc.) can inhibit production of foliage, fruit, or seeds, as well as reduce the quality and quantity of the harvested crop. Although most crops are treated with agricultural fingistats or-fungicides, fingal damage to agricultural crops typically results in revenue losses to the agricultural industry of millions of dollars annually.

Current control measures against plant fungal diseases include breeding cultivars for improved fungal resistance, cultural control, or the application of compounds or organisms that are toxic or otherwise antagonistic to the pathogen or towards the expression of disease symptoms.

These approaches have various problems that limit their effectiveness. For example, genetic resistance is often lacking in the desired commercial cultivars, while cultural methods, such as canopy management and reduced planting densities, are labor intensive and of limited efficacy. The application of synthetic fungicides for controlling plant fungal diseases may be expensive and have associated health risks.

The continuous economic toll taken by ph,topathogenic fungi suggests a need to develop new, more effective approaches for preventing fungal infection in plants. Additionally, these requirements should be met without significant adverse side effects to the plant or to the environment, and without seriously restricting planting or growth conditions, or requiring expensive chemical treatment of either growing plants or harvested fruit.

SUMMARY OF THE INVENTION

The present invention is based on the discovery of a new strain of Bacillus subtilis, designated herein as B. subtilis strain ATCC No. 55614, which is effective in inhibiting growth of plant pathogenic bacteria and fungi. The invention also encompasses a method for protecting a plant against fungal or bacterial infection by applying to the plant or its environment B. subtilis strain ATCC 55614, a supernatant obtained from a culture of the isolate, or a bioactive extract thereof.

In one aspect, the invention is directed to a biological culture of B. subtilis strain ATCC 55614. Various embodiments include a bioactive extract of B. subtilis strain ATCC 55614, a supernatant obtained from a culture of the isolate, and a composition containing one or more of the above. The composition may contain B. subtilis strain ATCC 55614 in an impure state or in the form of a biologically pure culture, and is effective to inhibit fingal and bacterial growth. In one particular embodiment, the composition is effective to inhibit growth of Botrytis cinerea. In yet another embodiment, the composition is effective to inhibit growth of Fusarium.

The present invention is also directed to a method for producing a B. subtilis extract having antimicrobial activity. In one particular embodiment of the method, the extract is isolated by extracting the cell culture medium of bacterial isolate ATCC 55614 to produce a crude extract, separating the crude extract on a solid support to produce separated fractions, screening the separated fractions for antifungal or antibacterial activity, and pooling the active fractions. In yet another aspect, the invention provides a method of protecting a plant against fungal or bacterial infection by applying a composition containing Bacillus subtilis strain ATCC 55614, a supernatant or an extract thereof to a plant or its environment.

In one embodiment, infectable surfaces of a plant susceptible to fingal or bacterial disease are coated with Bacillus subtilis strain ATCC 55614, a supernatant or an extract thereof. The invention thus provides a method for protecting a plant against infection caused by various plant phytopathogenic flimgi, e.g., Diplodia, Drechslera, Fusarium, Geotrichum, Sclerotinia, Sclerotium, Erysiphe, Podosphaera, Uncinula, Puccinia, Plasmopara and Stemphylium.

In yet another embodiment, a method for inhibiting Botrytis cinerea or Fusarium infection in a plant is provided. Related embodiments include a method. for inhibiting growth of vegetative hyphae, and for inhibiting the formation of sclerotia by B. cinerea or Fusarium, by applying a composition containing Bacillus subtilis strain ATCC 55614 or an extract thereof, to a plant or its environment. Also provided is a method of inhibiting germination of conidia of B. cinerea or Fusarium.

The methods of the invention are usefuil for protecting fruit-bearing plants, vegetable plants, flowering plants, and their associated post-harvest crops, against fungal or bacterial infection.

These and other objects and features of the invention will be more fildly appreciated when the following detailed description of the invention is read in conjunction with the accompanying drawings.

DETAILED DESCRIPTION OF THE INVENTION

I. Definitions

Figure 1A:
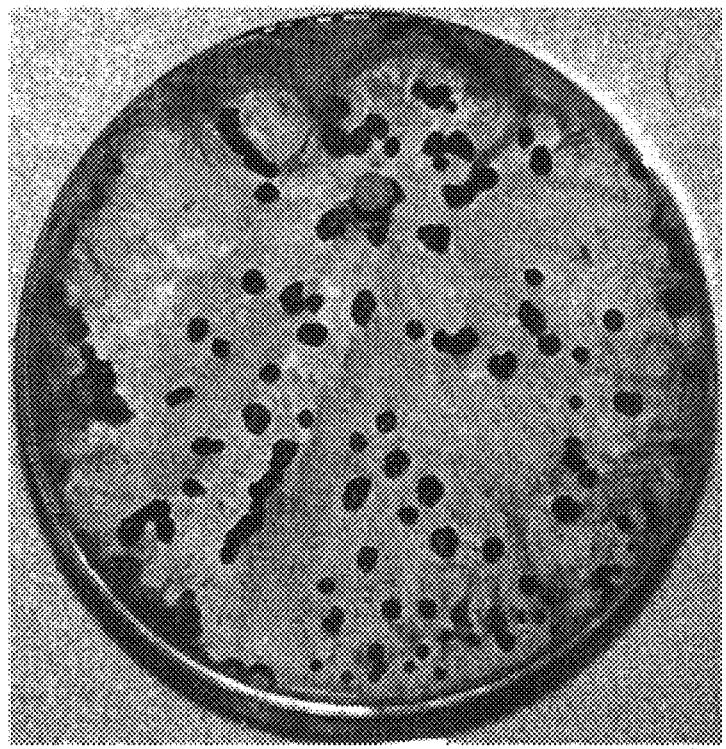
FIGS. 1A and 1B are computer generated photographs of PDA plates containing B. cinerea alone (FIG. 1A; negative control), and B. cinerea in combination with B. subtilis isolate ATCC 55614 (FIG. 1B)

"B. subtilis strain ATCC 55614" includes mutants and variants thereof, particularly mutants and variants effective to inhibit growth of soil or air-borne fungal pathogens from the division Deuteromycota (e.g., Botrytis sp.).

The microorganism, i.e., B. subtilis strain ATCC 55614, can be used in an impure state in combination with other materials which will not substantially interfere with the phytopathogenic fungi disease-suppressing characteristics of B. subtilis strain ATCC 55614, or in the form of a biologically pure culture.

By a "biologically pure culture" is meant a culture of the microorganism that does not include other materials (i) which are normally found in soil in which the microorganism grows, and/or (ii) from which the microorganism is isolated.

The term "culturing" refers to the propagation of organisms on or in media of various kinds. "Whole broth culture" refers to a liquid culture containing both cells and media "Supematant" refers to the liquid broth remaining when cells grown in broth are removed by centrifugation, filtration, sedimentation or other means well known in the art.

As. used herein, "biological control" is defmed as control of a pathogenic organism by the use of a second organism. Known mechanisms of biological control include enteric bacteria that control root rot by out-competing fungi for space on the surface of the root. Bacterial toxins, such as antibiotics, have been used to control pathogens. The toxin can be isolated and applied directly to the plant or the bacterial species may be administered so it produces the toxin in situ.

A "bioactive" extract of B. subtilis strain ATCC 55614 is one which possesses the antimicrobial properties of B. subtilis strain ATCC 55614, i.e., is capable of inhibiting growth of a microorganism. *B. subtilis* strain ATCC 55614 inhibits the growth of both bacteria and fingi.

A "microbial-suppressing amount" of *B. subtilis* strain ATCC 55614 or an active compound produced thereby is an amount sufficient to suppress growth of a phytopathogenic microorganism by at least about 50% in comparison to microbial growth for an untreated plant. Preferably, the microbial-suppressing amount will be sufficient to suppress from about 60%–80% of fungal or bacterial growth occurring on an untreated plant, and will depend upon various factors such as soil condition, climate, plant type, planting conditions and the like.

An "effective amount" is an amount sufficient to effect beneficial or desired results. An effective amount can be administered in one or more administrations. In terms of treatment and protection, an "effective amount" is that amount sufficient to palliate, ameliorate, stabilize, reverse, slow or delay the progression of fungal or bacterial disease states.

Plant, as defmed herein, includes any and all portions of a plant, including the root system, the shoot, including the stem, nodes, internodes, petiole, leaves, flowers, fruit, and the like, either prior to or post-harvest. Plant is also meant to include any cell derived from a plant, including undifferentiated tissue (e.g., callus) as well as plant seeds, pollen, progagules and embryos.

By "flowering plant" is meant any angiosperm. Examples of angiosperms include nearly all of the plants that have been domesticated for agriculture, such as wheat, maize, beans, rice, oats, potatoes and soybeans, as well as ornamentals.

"Ornamental flowering plant" is meant to include flowering omamentals such as orchids, petunias, zinnias, asters, begonia, geranium, lily, African violet and rose.

"Fruit-bearng plant" encompasses fruit-producing plants such as strawberry, raspberry, grapevine, tomato, pepper, cucumber, squash, melon, cantaloupe, watermelon, apple, peach, plum, nectarine, pear, sweetsop, cherimoya, banana, avocado, currant, persimmon, papaya, mango, guava and kiwifruit.

A "vegetable plant" is one which produces vegetables; examples of such plants include bean, beet, carrot, potato, spinach, celery, broccoli, cauliflower, cabbage and lettuce.

II. Isolation and Identification of *B. subtilis* Strain ATCC 55614

The present invention is based upon the discovery of a unique strain of *B. subtilis*, a spore-forming, aerobic, flagellate bacterium, which exhibits potent antifungal and antibacterial properties against a wide range of bacteria and filamentous and non-filamentous fungi. The isolation and identification of *B. subtilis* strain ATCC 55614, will now be described.

A. Source of *B. subtilis* strain ATCC 55614 and Preliminary Screening for Antimycotic Activity The microorganism of the present invention, a strain of *Bacillus subtilis*, can be obtained from soil or from plant hosts. Preferred sources of the bacterium are rhizosphere soil and root tissue from a raspberry plant. One particularly preferred plant host is the raspberry cultivar, cv Meeker. By way of example, the collection and isolation of bacterial samples for antimycotic screening, which led to the discovery of the unique strain of Bacillus described herein, is presented in Example 1.

Once a plant host and/or soil sample is obtained, bacteria associated with the sample is isolated and cultured as follows. The sample is typically washed with sterile water, soaked in phosphate buffered saline (PBS) solution, or surface sterilized. In cases where the bacterial is obtained from plant tissue, the tissue is typically chopped up and streaked onto agar medium, typically with a wire loop.

A number of different common agar media can be used to culture the bacteria, such as nutrient glucose agar (NDA; Difco, Detroit, Mich.), yeast extract-dextrose-calcium carbonate, nutrient-broth yeast extract agar (NBY), and Kings' medium B agar (KB), potato dextrose agar (PDA), the recipes for which are provided in Schaad (Schaad, 1988, page 3). Colonies typically appear on the medium in about 1–5 days.

These colonies are then assayed for antimycotic and antibacterial activity, to identify colonies producing compounds having antimicrobial activity. Any of a number of preliminary screening assays can be employed to determine antimycotic activity for the colonies of bacteria. One such assay, referred to herein as a streak test, is conducted by first streaking single colonies of bacterial isolates on suitable agar media, such as PDA. The sample is incubated for about 2–5 days, followed by addition of a plug of fungal pathogen to the previously incubated culture, at a specified distance from the bacterial streaks. The resulting culture is then examined for areas in which growth of pathogen is inhibited. One representative fungal pathogen against which the isolates can be screened is Botrytis, e.g., *Botrytis cinerea*. Additional exemplary fungal pathogens against which antifungal activity can be preliminarily assessed, such as by spot testing, include Fusarium, Diploditz Drechslera, Fusarium, Geotrichum, Sclerotinia, Sclerotium, Erysiphe, Podosphaera, Uncinula, Puccinia, Plasmopara and Stemphylium.

By way of example, screening of bacterial isolates obtained as described above resulted in the initial identification of several isolates capable of inhibiting mycelial growth of *B. cinera* (Example 2). The tests were performed on two different media, potato dextrose agar (PDA) and 25% tropic soy agar (TSA). Out of 1211 bacterial isolates tested, 12 were identified as inhibiting mycelial growth of *B. cinerea* by at least 50% in comparison to growth of *B. cinerea* under control conditions.

In additional screening experiments to evaluate the antagonistic effect of each of the 12 isolates on another fungal pathogen, Fusarium sp., only 1 of the isolates identified as inhibiting growth of *B. cinerea* severely limited growth of Fusarium sp.

Based upon its ability to severely inhibit growth of *B. cinerea* on both PDA and 25% TSA media, and its ability to effectively inhibit growth of Fusarium, this isolate, designated strain ATCC 55614, was chosen for further evaluation. The results of relevant in vitro screening assays are described in Examples 2 and 3. To summarize the results presented therein, strain ATCC 55614 was effective in inhibiting the growth of the fungal pathogen *Botrytis cinerea* by about 70% on both PDA and TSA media in comparison to untreated controls.

Another screening assay that can be used to identify isolates effective to inhibit growth of various pathogenic fuingi is a spot test or overlay test (Gross and Devay, 1977; Gross, et al., 1977). In conducting an overlay test, cells from a single colony are spotted onto an agar-containing plate (e.g., PDA) and incubated as described above. The colonies are then typically removed with a sterile swab and the plate is exposed to chloroform vapors for an extended period of time (e.g., 20 minutes) followed by dissipation of the chloroform vapors to kill remanig bacterial cells. To identify an isolate possessing antifuingal activity, the plate is oversprayed with a spore suspension of flimgal pathogen, and then examined for areas in which growth of fuingal pathogen is inhibited. Representative flungi against which antiflingal activity can be preliminarily assessed, such as by spot testing, include but are not limited to those described above, ie., Botryis, Diplodia, Drechslera, Fusarium, Geotrichum, Scierotinia, Scierotium and Stemphylium. A bacterial isolate is considered to be antagonistic against the growth of a given microbial pathogen if growth of the target phytopathogenic microbe is palliated ameliorated, stabilized, reversed, slowed or delayed, and preferably, if the progression of fuingal or bacterial disease states inhibited by at least about 50 percent in comparison to microbial growth in the absence of the bacteria.

After identifying a culture that is active in spot tests (e.g., isolate ATCC 55614), the bacterial strain is then further chrraracterized. Based upon a number of diagnostic tests described in Example 4, bacterial isolate ATCC 55614 was characterized as *Bacillus subtilis*. Diagnostic tests for determining the identity of a bacterial isolate are described generally below.

B. Features of *B. subtills* strain ATCC 55614

Bacteria belonging to the species *B. subtilis* possess a number of characteristic features, which have been described in detail in Schroth, et al. (1983) and in Schaad (1988) and are representative of *B. subtilis* strain ATCC 55614.

Characteristic features of *B. subtilis* are described briefly below.

1. LOPAT Testing. LOPAT tests (Levan formation, Oxidase test, Potato rotting ability, Arginine dehydrolase production, and Tobacco hypersensitivity) (Schaad, 1988) are usefid for determining a number of identifying features of a bacterial isolate. Bacteria belonging to the species *B. subtilis* will, on the whole, exhibit LOPAT characteristics as described in Scaaad.

2. Additional Diagnostic Tests. Once an isolate has been preliminarily identified as *B. subtilis* (ie., by LOPAT tests), a positive identification is made by submitting the isolate to additional diagnostic tests according to conventional diagnostic test protocols common in the art, as described in Schaad (1988).

Typically, secondary testing is then carried out, the results of which are based upon an isolate's ability to utilize a particular substrate or form a particular product. By way of example, the identity of isolate ATCC 55614 was confirmed by GC-FAME analysis and Biolog MicroPlateÔ (Biolog, Hayward, Calif.) analysis, which provides a standardized microtest method using 95 different tests to identify a broad range of enteric, non-fermenting, Gram-negative bacteria The microplate testing method examines the ability of bacteria to utilize or oxidize a preselected panel of different carbon sources, as described in GN MICROPLATE INSTRUCTIONS FOR USE, BIOLOG, Hayward, Calif. September 1993.

Based upon these testing results, bacterial isolate strain ATCC 55614 was identified as *B. subtilis*, as described in Example 4. *B. subtilis* ATCC 55614 has been deposited with the American Type Culture Collection (ATCC), 12301 Parklawn Drive, Rockville, Md. 20852, and assigned the following designation, ATCC 55614. The deposit was accepted by the International Depository Authority on Sep. 21, 1994.

3. Impact on Fungal-Induced Disease Manifestations. Experiments carried out in support of the invention indicate that *B. subtilis* strain ATCC 55614 is effective in inhibiting not only the growth of vegetative hyphae, but also in inhibiting sclerotia formation, e.g., by *B. cinerea* (Examples 3 and 5, respectively).

Referring to the exemplary in-vitro results presented in Table 2 from Example 5, column 2 (Range #), the absolute number of sclerotia for a *B. subtilis* strain ATCC 55614-treated sample was greatly reduced from that of an untreated control sample (no bacterial treatment). Based upon the mean values in column 3, an approximate 75–80% reduction in scierotia growth was observed in samples treated with *B. subtilis* strain ATCC 55614 when compared to control samples lacling the bacterial antagonist.

To determine whether the reduction was simply due to a reduction in growth of vegetative mycelia, the data was also calculated as a ratio of mycelial growth to the number of sclerotia. If the reduction in sclerotia for the treated sample was simply a result of a reduced number of mycelia, the ratios for the control and *B. subtilis*-treated sample would be expected to be similar. Based upon the mean values presented in column 5 of Table 2, the ratio for the treated sample is greater than for the corresponding control. This result indicates a decrease in sclerotia for a given number of mycelia (smaller denorinator), and thus a greater value for the overall ratio in comparison to the control. These results indicate that the Bacillus isolate of the invention is effective in inhibiting not only the growth of vegetative hyphae, but also in inhibiting sclerotia formation, e.g., by *B. cinerea*.

Additionally, *B. subtilis* isolate ATCC 55614 is effective in inhibiting germination of conidia of a fungal pathogen, e.g., *B. cinerea*, as supported by the illustrative results presented in Example 6. Conidia, which are produced by mycelium, are the primary source of inoculum in the field. The conidia (or spores) landing on or near a plant, germinate to produce mycelia, which then produce conidiophores with conidia, leading to growth of the fungus and the development of disease.

Figure 2A:
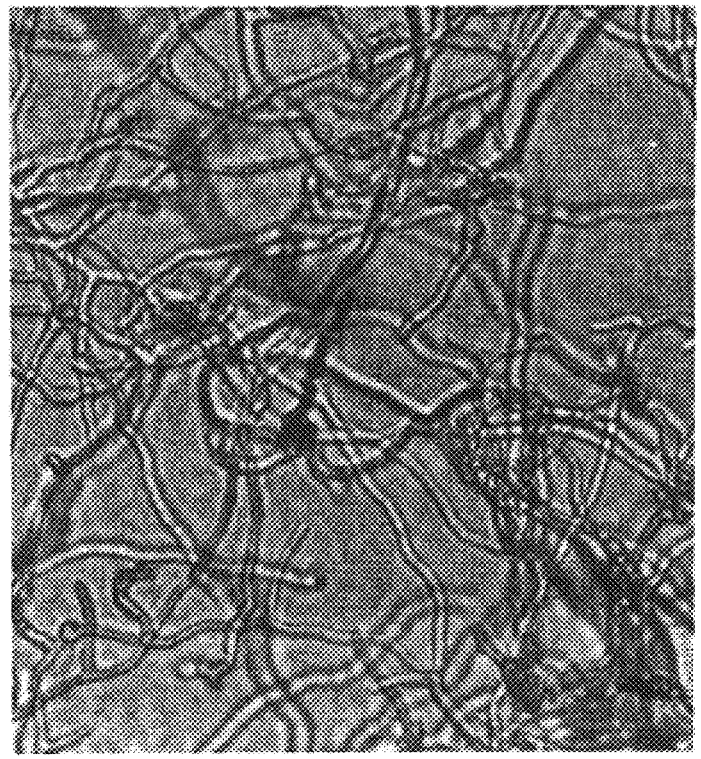
FIGS. 2A and 2B show computer generated photomicrographs of conidial germination on a control PDA plate (FIG. 2A) and on a PDA plate containing a streak of B. subtilis ATCC 55614 (FIG. 2B)
Figure 2B:
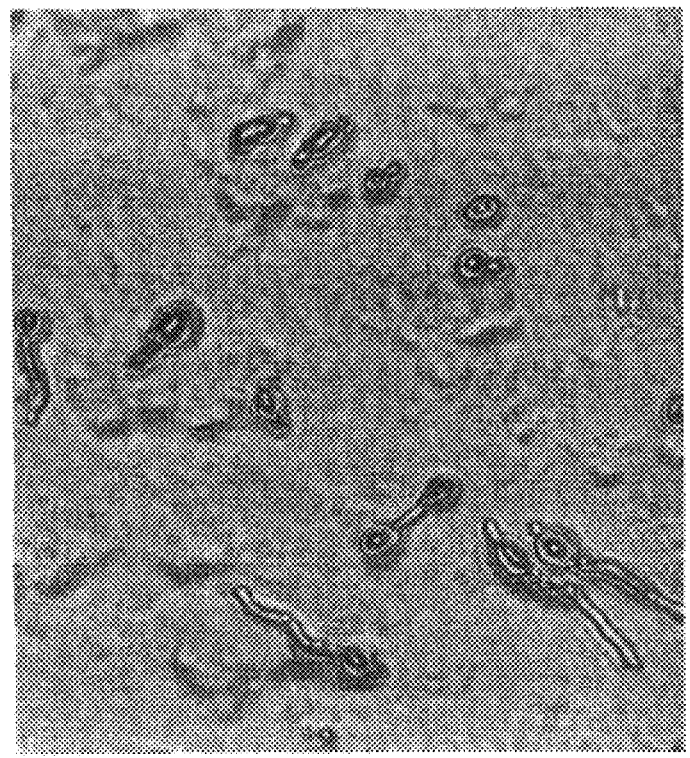

As described in detail in Example 6, conidia from *B. cinerea* were isolated and used to prepare a conidial suspension. The suspension was added to agar plates both with and without *B. subtilis* ATCC 55614, followed by incubation. The extent of germination was then evaluated by light microscopy (FIGS. 2A and 2B). The results are summarized in Table 3. In comparing the photomicrographs presented in FIGS. 2A and 2B, it can be seen that germination was inhibited by about 85 percent in the presence of *B. subtilis* ATCC 55614, in comparison to a control sample.

III. Isolation of a Bioactive Extract of *B. subtilis* Strain ATCC 55614

A. Separation of the Bioactive Component

As discussed above, the composition of the invention may contain *B. subtilis* strain ATCC 55614, a culture supernatant or an extract thereof. In compositions containing an extract of *B. subtilis* strain ATCC 55614 or a bioactive extract produced by the isolate, the isolate is typically at least partially purified away from cellular components, to provide an extract having antimicrobial activity as described in section II above.

A bioactive extract produced by *B. subtilis* strain ATCC 55614 is obtained generally as follows.

Typically, *B. subtilis* strain ATCC 55614 is grown in potato dextrose broth, or Antibiotic Medium 3 (Difco Laboratories (Detroit, Mich.) as stationary cultures for a period of several days. The culture medium is then extracted with a suitable solvent, e.g., ethyl acetate, chloroform, acetone, to remove various contaminating materials and obtain a bioactive extract. The resulting bioactive extract can be fuither separated by any of a number of common separation techniques, such as adsorption chromatography. Suitable solid support materials for chromatographic-based separations include gel filtration supports such as DEAE, C-18, for reverse phase applications, and XAD-type non-ionic supports. Recovered fractions are assayed for antifungal activity, such as by spot testing as described previously. Fractions exhibiting bioactivity are then pooled, and may be concentrated into dry form.

The resulting semi-purified preparation containing a bioactive component may then be used directly for treating fungal or bacterial infection, such as in topical applications (e.g., to inhibit fingal or bacterial growth in plants).

IV. Compositions Containing *B. subtilis* Strain ATCC 55614

A. Antifungal Formulations

Compositions containing *B. subtilis* strain ATCC 55614 may contain the isolate (i) in an impure state (e.g., culture broth) in combination with other, materials which will not adversely impact the phytopathogenic -disease suppressing characteristics of the isolate, nor adversely affect the health of the target plant or surrounding environment, (ii) as a biologically pure culture, (iii) a supernatant, or (iv) as an extract. The composition may include bioactive component mutants and variants of *B. subtilis* strain ATCC 55614, or a mixture thereof, particularly mutants and variants exhibiting phytopathogenic disease-suppressing characteristics that are substantially the same or improved over *B. subtilis* strain ATCC 55614. To prepare such a composition, *Bacillus subtilis* strain ATCC 55614 is grown using conventional techniques as described previously. Cultivation of *B. subtilis* can be carried out in either liquid or in solid nutrient media at a temperature of about 220–300° C. If limited amounts of the microorganism are desired, surface cultures and bottles may be employed.

The microorganism is typically grown in a nutrient medium containing a carbon source, such as, an assimilable carbohydrate, and a nitrogen source, e.g., an assimilable nitrogen compound or proteinaceous material. Representative carbon sources include glucose, brown sugar, sucrose, starch, lactose, and the like. Representative nitrogen sources include yeast, soybean meal, cornmeal, milk solids, and such. Trace metals (e.g., zinc, magnesium, cobalt, iron) may optionally be added to the fermentation media.

If a large quantity of the microorganism is required, a vegetative inoculum in a nutrient broth culture is typically prepared, e.g., by inoculating the broth culture with an aliquot from a soil, root tissue, or slant culture, and transferred aseptically to a large vessel or tank.

The optimum amounts of *Bacillus subtilis* strain ATCC 55614 endospores employed in the plant treatment composition herein for a particular application can be readily determined by those skilled in the art. In general, the active ingredient portion of a composition in accordance with the invention can contain from about 0.001% to about 50% by weight, and preferably from about 0.01% to about 30% by weight, of *Bacillus subtilis* endospores.

The composition of the present invention may contain one or more biologically inert components, e.g., carrier materials such as talc, gypsum, kaolin, attapulgite, wood flour, and/or binders such as ethylene glycol, mineral oil, polypropylene glycol, polyvinylacetate, nutrients, and plant growth hormones.

The antimicrobial composition can be formulated into a variety of formulations including powder, aqueous, flowable, dry flowable, or granular applications. The composition may also be microencapsulated. Powder formulations are generally prepared by mixing together the dry components. including any carrier and/or other additive(s), until a homogeneous mixture is formed. A binder, if employed, may then be added and the entire mass mixed again until it has become essentially uniform in composition.

A liquid formation, may, for example, include organic solvents such as xylene, methanol, ethylene glycol and mineral oil. Additional components may include surface active agents, e.g., calcium dodecylbenzenesulfonate, polyglycol ether, ethoxylated alkyl phenol or alkyl aryl sulfonates. Alternatively, the liquid formulation may be a aqueous-based suspension. Such formulations will typically contain about $10^6$–$10^9$ colony forming units (CFU) of *B. subtilis* strain ATCC 55614 per ml of aqueous carrier. In addition to containing water, an aqueous carrier may optionally contain a wax such as paraffin wax.

For granular applications, the carrier can be an inorganic or organic material. Representative examples include attapulgite, montmorillonite, bentonite, wood flour, starch, cellulose, bran, etc. The formulation may also include a binder such as mineral oil, lignosulfonate, polyvinyl alcohol or sucrose, to maintain granular integrity.

Moreover, the composition of the invention can be used together with one or more additional fungicidal or pesticidal materials. Exemplary insecticides for inclusion in the composition are, for example, organochlorine compounds such as lindane (1,2,3,4,5,6-hexachlorocyclohexane (garnma isomer)); organophosphoric esters such as diazinon (0,0-diethyl 0-2-isopropyl-6-methylpyrimidin-4-yl phosphorothioate), isazofos (0-5-chloro-1-isopropyl-1H-1, 2,4-triazol-3-yl-0,0-diethyl phosphorothioate), thiofanox (1-(2,2-dimethyl-1-methylthiomethylpropylideneaminooxy)-N-methylformamide), and the like; carbamates such as carbofiran (2,3-dihydro-2,2-dimethylbenzofuran-7-yl methylcarbomate), mercaptodimethur (3,5-dimethyl-4-(methylthio) phenol methyl carbamate), bendiocarb (2,2-dimethyl-1,3-benzodioxol-4-yl methylcarbamate); repellants such as anthraquinone, thioanthraquinone, benzathrone, ziram (zinc bis(dimethyldithiocarbomate)) and diphenylguaaidine.

In general, the *Bacillus subtilis* ATCC 55614 endospore component of a composition of the invention will typically retain at least about 50, and preferably at least about 70 percent of its original viability after storage of the composition for a period of up to about 36 months.

B. Method of Preventing Fungal or Bacterial Growth

The method of the present invention comprises applying to plants an effective amount of the biocontrol composition described herein. The composition can be utilized for either field or post harvest application. The composition can be applied to any portion of a plant including its foliage, fruit, root system, or may be employed as a seed dressing. When employed as a seed dressing, the composition is generally applied to seed at a rate of from about 125 to about 2000 grams, and preferably at a rate of from about 250 to about 750 grams per 100 kilograms of seed.

In one approach for preventing fungal or bacterial growth in plants, *B. subtilis* strain ATCC 55614 is used to coat injectable surfaces of a plant susceptible to fungal- or bacterial-promoted disease. For such topical applications, the isolate will typically be formulated either as a liquid (for spray applications), an aerosol, or powder (for dusting injectable plant surfaces) as described above. Alternatively, the strain may be used for systemic treatment of plant fungal diseases, for uptake by the root system. In such cases, the isolate is typically formulated as granules, usually for convenience in application. Granule formulations are typically activated by application of water, and release of active compound typically occurs over an extended period of time, such as from 2–12 weeks. As the following examples demonstrate, plant protecting compositions in accordance with the invention exhibit potent protection against phytopathogenic fumgi, particularly Botrytis, Phytophthora, Pythium, Rizoctonia, Alternaria, Monilinia and Fusarium, and also against the gram-negative bacterium, Erwinia.

According to another aspect of the invention, a method is provided for forming a fungal- or bacterial-resistant transgenic plant. The transgenic plant contains a chimeric gene corresponding to the gene attributable to the antagonistic phenotype of B. subtilis strain ATCC 55614. The chimeric gene is operably linked to a plant-compatible promoter effective to drive expression of the chirneric gene, and encodes a product effective to confer resistance to a fungal or bacterial pathogen (e.g., Botrytis, Fusarium) in transformed plant cells.

Briefly, in carrying out the method, a genetic locus attributable to the antagonistic phenotype of B. subtilis strain ATCC 55614 is first identified, e.g. by mutagenesis of B. subtilis. Prior to mutagenesis, the ability of wildtype B. subtilis strain ATCC 55614 to antagonize growth of B. cinerea is confirmed. Mutagenis of B. subtilis is then carried out according to standard protocols. Following mutagenesis, mutants are assayed for their ability to inhibit vegetative mycelial growth essentially as described above and in Example 2. Putative mutants deficient in antagonism against B. cinerea are then used to identify a genetic locus attributable to the antagonistic phenotype of B. subtilis ATCC 55614.

Upon identification, cloning, and sequencing of the gene, the transgene can then be used to form a transgenic plant in which expression of the transgene is effective to confer resistance to a fungal pathogen (e.g., Botrytis, Fusarium) to the plant. Additionally, the transgene may be introduced into a prokaryotic or eukaryotic organism to form a recombinant organism capable of producing the above-described antifungal compound secreted by B. subtilis strain ATCC 55614.

V. Utility

Experiments conducted in support of the invention demonstrate that B. subtilis strain ATCC 55614 is effective in inhibiting growth of plant pathogenic fungi including but not limited to Botrytis, Phytophthora, Pseudomonas, Erwinia, Alternaria, Trichoderma, Monilinia, Puccinia, Rhizoctonia, Phythium and Plasmopara and Fusarium, and is also effective for preventing the development of plant diseases associated with these pathogens.

The bioactive strain can be used to treat plant diseases such as seedling damping off and root rot disease, vascular wilt diseases, or any disease state caused by attack of one of the above-described flngal or bacterial plant pathogens (e.g., Table 13).

The composition of the invention is useful for preventing Botrytis-related diseases such as grey mold of strawberry and raspberry, bunch rot of grapes, grey mold rot of vegetables such as bean, beet, carrot, and cucumber, tip-end rot of lettuce, pepper, tomato, and squash, dry eye rot disease in apple, and grey mold or blight of numerous ornamentals such as begonia. geranium, lily, African violet and rose. The composition can also be used to treat vascular wilt diseases induced by Fusarium, such as wilt diseases of tomato, peas, bananas and cotton.

The composition and method of the invention may be employed to protect commercial raspberry cultivars such as Canby, Chilcotin, Amity, and Willamette against grey mold. These cultivars are particularly susceptible to damage by grey mold caused by Botrytis. Similarly, the composition and method described herein can be used to protect commercial varieties of strawberry susceptible to attack by grey mold, e.g., Chandler, Pajaro, and Selva.

By way of example, greenhouse tests conducted in support of the invention (Example 7) revealed the effectiveness of B. subtilis strain ATCC 55614 in reducing losses in greenhouse grown strawberries (cv Pajaro) due to grey mold caused by B. cinerea. The details of the study are summarized briefly below.

In conducting the tests described in Example 7, strawberry plants inoculated with B. cinerea were subjected to various treatment regimes. The treatments included 5 foliar applications of (i) Rovral 50 VP, a commercially available fungicide used for controlling Botrytis fruit mold on strawberries, (ii) potato dextrose broth, (iii) B. subtilis strain ATCC 55614, and (iv) an untreated control series. The plants, including the flowers, were treated prior to inoculation.

Test results were evaluated based upon a number of factors, including numbers of healthy fruits, weight of healthy fruit recovered, weight of diseased fruit, and percent of total harvest weight attributable to diseased fruit. In examining the results provided in Tables 4, 5, 6, and 7, it can be seen that foliar treatment with a composition containing B. subtilis strain ATCC 55614 was effective in controlling fruit losses due to grey mold, as indicated by the quantity of diseased fruit expressed as a percentage of total harvest weight, for both treated and untreated (control) fruit. Additionally, treatment with B. subtilis strain ATCC 55614 did not adversely impact the yield (i.e., weight) of healthy strawberry fruit.

The antifungal composition described herein can also be applied to grape varieties such as White Riesling and Pinot Noir, Chardonnay, Zinfandel and Chenin blanc for preventing grey mold infection. These varieties are all susceptible to attack by B. cinerea (Pscheidt, 1990, 1991; 1993 PACIFIC NORTHWEST PLANT DISEASE CONTROL HANDBOOK; English, et al., 1989; Gubler, etal., 1987).

Experiments carried out in support of the invention also indicate that the Bacillus isolate of the invention is effective in inhibiting both (i) the growth of vegetative hyphae, and (ii) sclerotia formation, e.g., by B. cinerea (Examples 3 and 5, respectively).

One component of the disease cycle of B. cinerea on long lived perennial crops (e.g., grape and raspberry) is the production of sclerotia that overwinter on dead debris. The sclerotia germinate in the spring and initiate infection of the new growing season (Weller, 1988). Thus, application of a composition containing B. subtilis strain ATCC 55614, an extract or bioactive metabolite thereof, may be used for reducing the source of inoculum overwintering on dead, necrotic, or senescent tissue.

Another important component of the disease cycle of B. cinerea is the production of conidia. The conidia serve as a primary source of inoculum under field conditions. Experiments carried out in support of the invention indicate that B. subtilis isolate ATCC 55614 is also effective for inhibiting the germination of conidia of B. cinerea (Example 6). By inhibiting conidia germination, the compositions and methods described herein can be used as a preventative measure for reducing Botrytis-related losses.

Due to its effectiveness in inhibiting conidia germination, the antifungal composition may also serve as a control for disparate genera of phytopathogenic fungi that are members of the classes Ascomycota and Deuteromycota (Fungi imperfecti). Representative genera include Verticillium sp., Fusarium sp., Macrophomina sp., Thielaviopsis sp., and genera of fungi that are causal agents of downy mildew diseases.

Additionally, an antifungal composition comprising an extract produced by B. subtilis strain ATCC 55614 may be used to treat human fungal diseases in which the disseminated disease propagule is a conidia, for example, Aspergillus sp., Histoplasma sp., and Tinea sp.

The following examples illustrate, but in no way are intended to limit the present invention.

MATERIALS AND METHODS

Unless indicated otherwise, chemicals and reagents, e.g., potato dextrose agar (PDA), potato dextrose broth (PDB), tropic soy agar (TSA) and malt extract agar (MEA), were obtained from Sigma Chemical Company, St. Louis, Mo.

A. Fungal Cultures

Pure cultures of Botrytis cinerea (B. cinerea) were obtained from the American Type Culture Collection (ATCC; Rockville, Md.; Accession number 11542) and maintained at 25° C. on PDA.

EXAMPLE 1

Collection/Isolation of a Novel Bacterial Strain

Bacteria were isolated from rhizosphere soil and from root tissue of raspberry plants (cv. Meeker) located at Washington State University—ARS (Vancouver, Wash.).

Soil and root materials were placed in a test tube. Five volumes of phosphate saline buffer (PSB, pH 7.3; Wollum, 1982) were added and the tube was vortexed for 1 minute. A dilution series ($10^{-1}$ to $10^{-8}$) was made using PSB. One hundred 11 of each dilution was plated onto petri dishes containing PDA (*ATCC MEDIA HANDBOOK*, 1984). Plates were incubated at 200° C. in a growth chamber employing a 16 hour day length.

EXAMPLE 2

Screening of Bacterial Isolates for Antifungal Activity

Single colonies of bacterial isolates were streaked in a straight line approximately 12 mm from the edge of a 100 mm ' 15 mm petri dish (plate) containing PDA. The streaked plate was incubated for 2 days in a growth chamber as in Example 1 above. Following the 2 day incubation period, a 5 mm plug of B. cinerea hyphae grown on PDA was added to each plate approximately 55 mm from the edge of the bacterial streak closest to the center of the plate. Control plates lacking bacterial streaks were similarly inoculated to assess the growth of B. cinerea in the absence of bacteria. All plates were incubated as in Example 1 above.

Each bacterial isolate was initially tested twice for the ability to inhibit growth of B. cinerea. Putative antagonistic isolates were identified and retested on PDA plates, as well as on plates containing 25% tropic soy agar (TSA). Bacterial isolates identified in the initial screen as having antifungal activity were then retested using 10 replica plates of each PDA and 25% TSA, to determine the relative ability of each isolate to inhibit growth of B. cinerea.

Of 1211 bacterial isolates tested for antagonism against the growth of B. cinerea, twelve were identified as inhibiting mycelial growth of B. cinerea by at least 50% as compared to growth of B. cinerea under control conditions.

The 12 isolates shown to inhibit growth of B. cinerea were at least partially tested for their ability to inhibit growth of Fusarium sp. The tests were carried out essentially as described above for antagonism against B. cinerea, using PDA plates onto which a 5 mm hyphal plug of Fusarium sp. was introduced.

Of the 12 isolates, only one (later designated as B. subtilis strain ATCC 55614) severely limited gro,Nh of Fusarium.

Based upon the results of the in-vitro test, strain ATCC 55614 was essentially as effective as a known commercial biocontrol agent, "MYCOSTOP" (*Streptomyces griseoviridis* strain 61) in inhibiting growth of Fusarium sp.

Figure 5A:
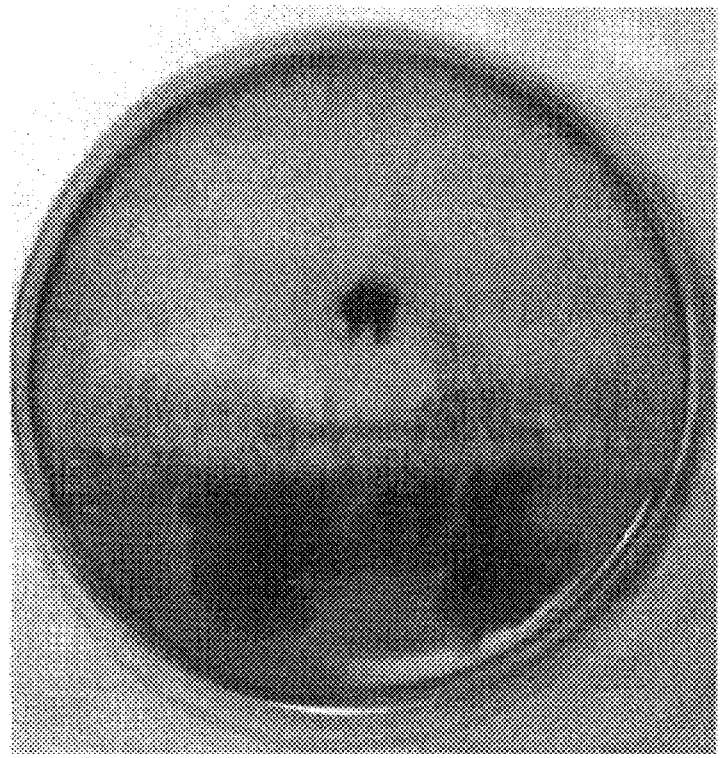
FIGS. 5A and 5B are computer generated photographs of PDA plates plated with Fusarium sp., and a commercial biocontrol agent, MYcosTOP (Streptomyces griseovinddis strain61) and Fusarium sp. and B. subtilis strain ATCC 55614, respectively.
Figure 5B:

The results are presented in FIGS. 5A and 5B.

EXAMPLE 3

Effects of Isolates on Hyphae Necrosis

Of the 12 isolates identified above, 1 was selected for further analysis based on its ability to severely inhibit growth of B. cinerea on both PDA and 25% TSA plates. This isolate was designated isolate ATCC 55614.

The effects of the isolate on B. cinerea mycelial growth was assayed as above, and results are summarized in Table 1, below. Antagonism towards Botrytis was evaluated by determining the extent of growth of the fingus, reported as the distance from the agar plug containing the inoculum. As can be determined from Table 1, larger numbers indicate a greater extent of fuingal growth, and thus a lesser degree of antifungal activity.

TABLE 1

| In vitro Antagonism of *Botrytis cinerea* Growth[1] | | | |
|---|---|---|---|
| Treatment | Media | Range (mm) | Growth (u + SD) |
| Control | PDA | 59–62 | 60.9 + 1.10 |
| Isolate ATCC 55614 | PDA | 15–19 | 17.5 + 1.35[2] |
| Control | TSA | 60–62 | 61.5 + 0.85 |
| Isolate ATCC 55614 | TSA | 17–21 | 18.7 + 1.57[2] |

The data presented in Table 1 indicate that isolate ATCC 55614 inhibited the growth of B. cinerea by 71.3% and 69.6% on PDA and TSA plates, respectively.

Figure 1B:
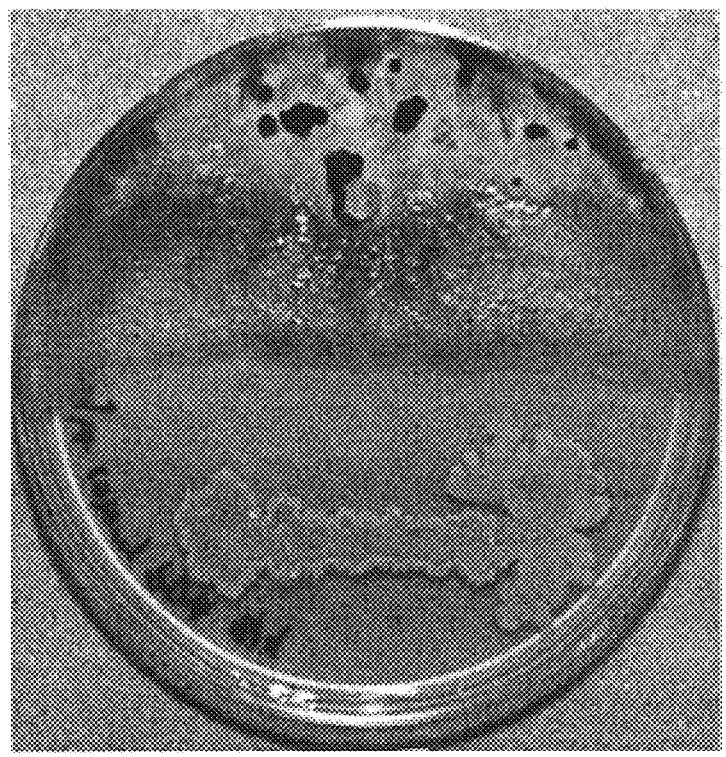

FIGS. 1A and 1B show computer generated photographs of PDA plates on which are plated B. cinerea and Isolate ATCC 55614 (FIG. 1B), and a negative control plate containing only B. cinerea (FIG. 1A). The images were obtained 14 days after application of a 5 mm hyphal plug of B. cinerea.

Maintenance of healthy B. cinerea hyphae was severely affected by the bacterial isolate. Necrosis of hyphae first became visible after about 5 days and continued in a linear fashion as hyphae nearest to the bacteria become necrotic, followed by necrosis of hyphae more distal to the bacterial streak. Very little mycelial growth (about 3 mm) having the cottony-white characteristics of healthy B. cinerea mycelia (FIG. 1A) was observed after 14 days in the plate containing isolate ATCC 55614.

EXAMPLE 4

Isolate Characterization and Species Identification

The isolate identified above as having activity against B. cinerea was further characterized using conventional methods for identifying plant pathogenic bacteria (Schaad. 1988).

Specifically, the identify of the isolate was determined using GC-FAME analysis and the Biolog Microtiter System. The Biolog Microtiter system is based upon an isolate's ability to utilize or oxidize a preselected panel of 96 different carbon sources using the GN MICROPLATEÔ test panel (Biolog, Hayward, Calif.), according to the manufacturer's recommended protocol (GN MicroplateÔ, Instructions for Use, Biolog, Inc., Hayward, Calif., 1993). Wells in which no reaction occurred remained colorless; positive results were indicated by the appearance of a purple color. The test results were processed using the MICROLOG 3Ô computer software program available through Biolog, Inc. (Hayward, Calif.), which automatically cross-references the pattern of purple wells to an extensive library of species.

Based upon these tests, isolate ATCC 55614, was identified as an antimycotic-producing strain of *Bacillus subtilis* (*B. subtilis*).

Bacterial isolate *B. subtilis* ATCC 55614 has been deposited with the American Type Culture Collection (ATCC), 12301 Parklawn Drive, Rockville, Md. 20852, and assigned an ATCC designation number 55614. The deposit was received by the ATCC on Sep. 21, 1994.

EXAMPLE 5

Sclerotia Assay

The effects of *B. subtilis* ATCC 55614 on sclerotia production were also examined. PDA plates (both with and without bacterial isolates) were inoculated with a 5 mm mycelial plug containing *B. cinerea* as described above. Sclerotia were counted 21 days after inoculation of the PDA plates.

Due to the observation of significantly diminished sclerotia production by *B. cinerea* on TSA media, the experiment was not carried out on TSA plates.

Sclerotia counting: Due to the possibility that any reduction in the number of sclerotia counted in the assay was a consequence of the reduction in growth of vegetative mycelia, the ratio of mycelial growth to the number of sclerotia was calculated for each condition.

Results of these studies are summarized in Table 2, below. Range (#) indicates the total number of sclerotia present on a plate, while the column with the heading Range represents the ratio of mycelial growth to number of sclerotia.

TABLE 2

Antagonistic Effects on Sclerotia Growth[1]

| | mm/# Sclerotia | | # Sclerotia Growth (mm)/#Sclerotia | |
|---|---|---|---|---|
| Treatment | Range (#) | (u + SD) | Range | (u + SD) |
| Control | 91–142 | 116 + 21.6 | 0.430–0.659 | 0.534 + 0.099 |
| *B. subtilis* | 19–28 | 24.6 + 4.2 | 0.679–0.842 | 0.726 + 0.079[2] |

[1]a. Sclerotia counted 21 days after inculation of PDA plate with a 5 mm mycelial plug.
b. Growth conditions = 20° C., 16 day period.
c. Mean and SD calculated for n = 5.
[2]Means are significantly different than control (alpha = 0.01).

The data demonstrate that bacterial isolate *B. subtilis* ATCC 55614 reduced the number of sclerotia as compared to the negative control. Further, the inhibition of sclerotia production by *B. subtilis* cannot be a consequence of reduced mycelia growth, since the ratio of growth to the number of sclerotia is significantly different between the negative control and the treatment with *B. subtilis* (comparing, for example, the values in the last column).

Thus, the in vitro analyses described herein indicate that *B. subtilis* ATCC 55614 has the ability not only to inhibit growth of vegetative hyphae, but also to inhibit the formation of scierotia by *B. cinerea*.

EXAMPLE 6

Conidia Assay

The impact of *B. subtilis* ATCC 55614 on another aspect of the disease cycle of *B. cinerea*, i. e., the production of conidia, was also conducted. Conidia serves as the primary source of inoculum for disease under field conditions.

Conidia were produced in culture by growing *B. cinerea* on malt extract agar (MEA) for 5 days at 25° C. with a 12 hr day length, followed by exposing the plates to ultraviolet (UV) light for 3 days (Leifert, et al., 1993). The plates were then flooded with 10 ml double deionized $H_2O$ and the conidia were removed from conidiophores by gently scraping the plates with a rubber policeman. The liquid was pipetted from the plates and filtered 4 times through a double layer of cheesecloth. The resulting suspension was vortexed for 1 minute to separate the conidia into individual propagules. The density of conidia per ml of double deionized $H_2O$ was determined using a hemocytometer, and the suspension was diluted to achieve a stock concentration of 1.0 ' $10^5$ conidia/ml.

10 µl of the conidia suspension (approximately 1000 conidia) were plated onto PDA plates and incubated for 12 hr in the dark at 250° C. Another 10 µl of the suspension were placed on PDA plates on which a streak of *B. subtilis* ATCC 55614 had been grown for 2 days. The conidia suspension was placed 1 cm away from the bacterial streak and similarly incubated.

Germination was evaluated after 12 hr incubation in the dark at 28° C. The plates were observed under a light microscope (100×), and 100 conidia were evaluated on each plate for germination. Exemplary photomicrographs of conidial germination obtained in this experiment are presented in FIGS. 2A and 2B. The image in FIG. 2A illustrates complete germination of conidia on control PDA plates. The image in FIG. 2B presents an example of inhibition of germination of conidia that were placed 1 cm away from the streak of *B. subtilis*.

Results from these experiments are summarized in Table 3, below.

TABLE 3

Conidia Germination Assays[1]

| Treatment | Mean Germination (%) |
|---|---|
| *B. subtilis* | 14.2 ± 5.26 |
| Control | 99.2 ± 1.79 |

[1]Approximately 1000 conidia were placed 1 cm away from a 2-day old streak of each biocontrol agent Potato Dextrose Agar. Plates were incubated overnight at 25° C. 100 conidia per plate were randomly assayed for germination. The experiment was repeated 5 times.

The results in Table 3 demonstrate the effectiveness of *B. subtilis* ATCC 55614 to inhibit germination of conidia of *B. cinerea*.

EXAMPLE 7

Greenhouse Tests

Greenhouse tests were conducted to determine the effectiveness of *Bacillus subtilis* ATCC 55614 in controlling losses in greenhouse-grown strawberries (cv. Pajaro) due to grey mold caused by *Botrytis cinerea*.

The efficacy of *B. subtilis* ATCC 55614 was compared to: (i) a foliar application of PDB alone (negative control), and (ii) Rovral 50 WP ("IPRODIONE"; Rhone-Polenc, Paris, France), a commercially available and widely used fungicide for the control of Botrytis fruit mold on strawberries.

A. Growth of Strawberries

Strawberry plants (cv. Pajaro) were obtained as rooted crowns from BHN Research (Watsonville, Calif.). The plants were potted into 6" plastic pots (one plant/pot) filled with BlackGold 100% organic soil (BlackGold, Inc., Hubbard, Oreg.). Plants were watered, fertilized regularly with Peters 20:20:20 fertilizer and grown under an 18 hour light/6 hours dark cycle.

B. Bacterial Cultures

Single colonies of *B. subtilis* ATCC 55614 were used to inoculate two, 2 L flasks containing PDB (1 liter/flask). The flasks were placed in a rotary shaker and grown for 48 hours at 28° C., 225 rpm. Cell density was measured by absorbance at 600 nm using a spectrophotometer. Based on this reading, the cultures were adjusted with PDB to a final cell density of approximately $5 \times 10^{-8}$ cells/nil.

C. Treatments

Treatments included foliar applications of (i) Rovral 50 VP at 1.5 lb/100 gallons water, (ii) no treatment (control), (iii) PDB alone, or (iv) *Bacillus subtilis* strain ATCC 55614 ($5 \times 10^{-8}$) CFU/ml in PDB).

The treatments were administered by spraying plants with a hand sprayer containing one of the above compositions. Plants were sprayed to run-off (approximately 75 ml/plant). Treatments (i) through (iv) were applied 5 times during the test. The first application was at 10% flower bloom and the next four were at two week intervals thereafter. The fifth treatment was applied one day before the first harvest.

D. Artificial Greenhouse Inoculation of Strawberry Plants with *B. cinerea*

Plants were inoculated with *B. cinerea* by spraying to run-off with a $4 \times 10^{-3}$ conidia/ml suspension (approximately 75 ml/plant) in three spraying sessions. The first spraying was administered on the day that the first inflorescence was observed, and the next two were administered at two week intervals thereafter.

E. Harvesting

All ripe berries were harvested from all plants, once per week, for three consecutive weeks. The first harvest was the day following the last treatment.

F. Sample Size

Treatments were conducted on "blocks" of 5 plants each and each treatment was replicated 4 times (A, B, C, and D), resulting in 20 plants per treatment.

G. Parameters Evaluated

The following parameters were evaluated after each harvest: (i) number of healthy fruits, (ii) weight of healthy fruit (g), (iii) weight of diseased fruit (g), and (iv) percent of total harvest weight attributable to diseased fruit.

After evaluating the above parameters, healthy fruits were placed in plastic trays with individual compartments (such that the fruits did not contact one another) and the trays were covered with plastic wrap and stored at 4° C. for 7 days. This 4° C., 95% relative humidity (RH) treatment was to mimic storage conditions in the wholesale/retail distribution chain.

After 7 days storage at 4° C., 95% RH healthy fruits were evaluated as above for (i) weight of healthy fruit (g), (ii) weight of diseased fruit (g), and (iii) percent of total harvest weight attributable to diseased fruit.

The following equation was used to determine the percent of total harvest weight attributable to diseased fruit:

$$\frac{(g) \text{ diseased fruit } (T=0) + (g) \text{ diseased fruit } (T=7)}{(g) \text{ healthy fruit } (T=7) + \sum_{T=0}^{7} (g) \text{ diseased fruit}}$$

H. Results

Exemplary results of the greenhouse tests are summarized in Tables 4, 5, 6 and 7, and FIGS. 3A, 3B, 4A and 4B.

Figure 3A:
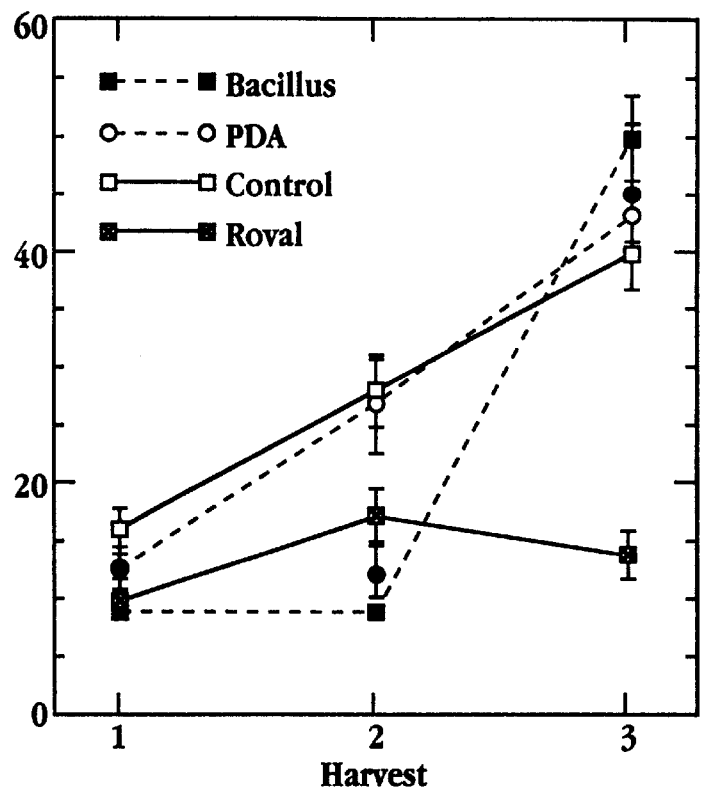
FIGS. 3A and 3B show the percentage of total harvest weight due to diseased fruit (y-axis), at harvest time (FIG. 3A), and after storage at 40° C. for 7 days under 95% RH (FIG. 3B), in harvests 1, 2 and 3 (x-axis) for fruit receiving various treatments (indicated)

Table 4 shows the percentage of total harvest weight due to diseased fruit at harvest time (T=0), in harvests 1, 2 and 3, for control fruit and fruit treated with Rovral or *B. subtilis* ATCC 55614. These results are also presented graphically in FIG. 3A. The y-axis in FIG. 3A shows the percent of harvest weight due to diseased fruit at each of three harvests (1, 2 and 3) indicated on the x-axis.

TABLE 4

Diseased Fruit as Percentage of Harvest Weight at Harvest Time

| Treatment | HARVEST 1 Mean ± S.E. | HARVEST 2 Mean ± S.E. | HARVEST 3 Mean ± S.E. |
|---|---|---|---|
| Rovral | 9.13 ± 0.54 | 17.20 ± 2.40 | 13.79 ± 2.22 |
| Control | 15.86 ± 1.74 | 28.01 ± 2.96 | 40.46 ± 3.17 |
| PDB | 12.53 ± 1.08 | 27.01 ± 4.33 | 43.65 ± 2.91 |
| Bacillus | 8.51 ± 0.82 | 8.60 ± 0.76 | 50.06 ± 3.50 |

At the first harvest, the mean weight (and percent of total) of diseased fruit treated with Rovral and *B. subtilis* ATCC 55614 was significantly less than the control treatment. At the second harvest, the data segregated into two subgroups. The mean weight (and percent of total) of diseased fruit from samples treated with Rovral or Bacillus was significantly less than the weight and percentage of diseased fruit from samples that had received either no treatment (control), or samples treated only with PDB. No significant differences were observed within the two subgroups. At the third harvest, the mean percentage of diseased fruit was significantly less in samples treated with Rovral than in samples receiving any of the other three treatments.

Figure 3B:
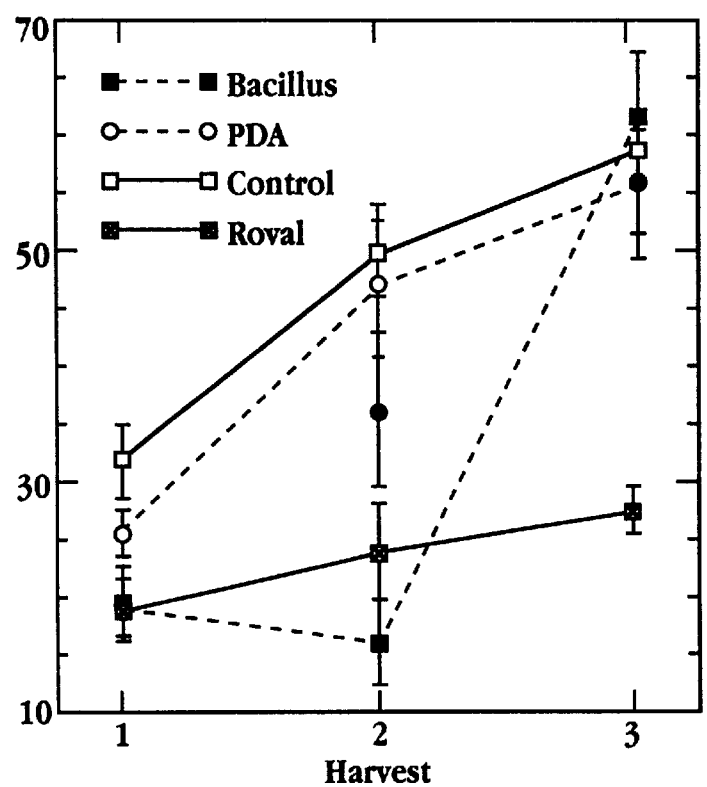

Table 5, below, shows the percentage of total harvest weight due to diseased fruit, after storage at 4° C. for 7 days under 95% RH (T=7), in harvests 1, 2 and 3 for control fruit and fruit treated with Rovral or *B. subtilis* ATCC 55614. These results are also presented graphically in FIG. 3B. The y-axis in FIG. 3B shows the percent of harvest weight due to diseased fruit at each of three harvests (1, 2 and 3) indicated on the x-axis.

TABLE 5

Diseased Fruit as Percentage of Harvest Weight After 7 Days Storage (4° C., 95% RH)

| Treatment | HARVEST 1 Mean ± S.E. | HARVEST 2 Mean ± S.E. | HARVEST 3 Mean ± S.E. |
|---|---|---|---|
| Rovral | 18.68 ± 0.44 | 24.35 ± 4.29 | 28.33 ± 2.26 |
| Control | 32.37 ± 3.33 | 50.55 ± 2.65 | 59.15 ± 1.94 |
| PDB | 25.85 ± 2.13 | 47.90 ± 6.58 | 56.56 ± 6.22 |
| Bacillus | 19.28 ± 2.58 | 16.12 ± 3.82 | 62.10 ± 5.23 |

At the first harvest, the mean weight (and percent of total) of diseased fruit treated with Rovral or Bacillus was significantly less than corresponding measurements from samples receiving control treatments. At the second harvest, the mean weight (and percent of total) of diseased fruit subjected to PDB and control treatments were significantly higher than corresponding measurements from samples receiving Rovral or Bacillus treatments. As was the case for samples examined immediately after harvest, the mean percentage of diseased fruit from the third harvest was significantly less in samples treated with Rovral than in samples receiving any of the other three treatments. No consistent significant differences were observed between control and PDB treatments in both freshly-analyzed and stored fruit.

Figure 4A:
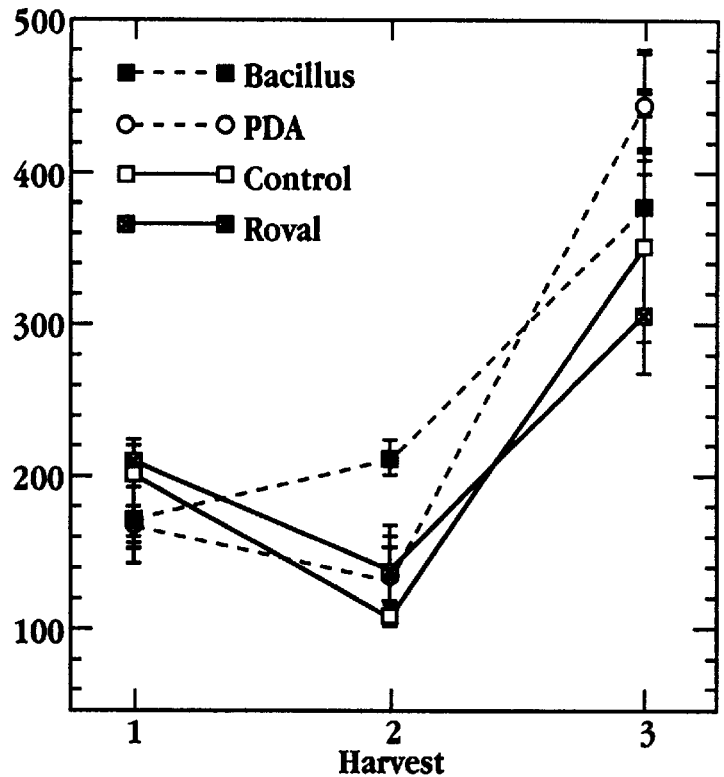
FIGS. 4A and 4B show the weight of healthy fruit (y-axis), at harvest time (FIG. 4A), and after storage at 40° C. for 7 days under 95% RH (FIG. 4B), in harvests 1, 2 and 3 (x-axis) for fruit receiving various treatments (indicated)

Table 6, below, shows the weight of healthy fruit, at harvest time (T=0), in harvests 1, 2 and 3 for control fruit and fruit treated with Rovral, or *B. subtilis* ATCC 55614. These results are also presented graphically in FIG. 4A. The y-axis in FIG. 4A shows the weight of healthy fruit (in grams) at each of three harvests (1, 2 and 3) indicated on the x-axis.

TABLE 6

Weight Healthy Fruit at Harvest Time

| Treatment | HARVEST 1 Mean ± S.E. | HARVEST 2 Mean ± S.E. | HARVEST 3 Mean ± S.E. |
|---|---|---|---|
| PDB | 165.23 ± 6.41 | 126.47 ± 20.52 | 432.25 ± 37.93 |
| Bacillus | 168.34 ± 21.38 | 209.14 ± 7.32 | 372.91 ± 30.71 |
| Control | 197.41 ± 21.09 | 100.86 ± 8.60 | 345.98 ± 61.42 |
| Rovral | 208.92 ± 14.79 | 131.88 ± 29.58 | 300.97 ± 38.21 |

At the first harvest, no significant differences were observed in the mean weight of healthy fruit receiving each of the four treatments. At the second harvest, the data segregated into two subgroups. The mean weight of healthy fruit from samples treated with Bacillus was significantly greater than the mean weight of healthy fruit from control, PDB or Rovral-treated samples, with no significant differences among treatments in either subgroup. At the third harvest, there were no other significant differences.

Figure 4B:
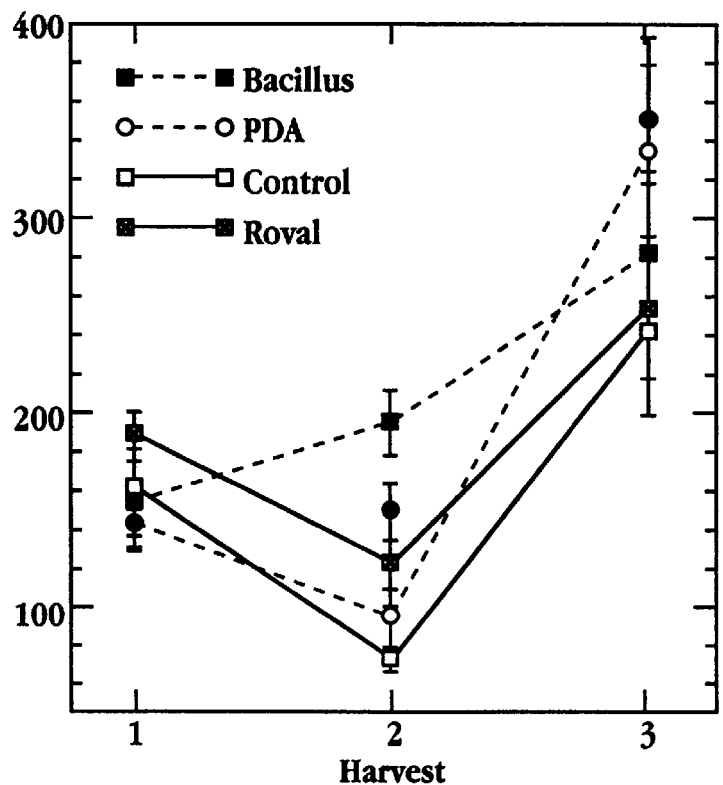

Table 7, below, shows the weight of healthy fruit, after storage at 4° C. for 7 days under 95% RH (T=7), in harvests 1, 2 and 3 for control fruit and fruit treated with Rovral or *B. subtilis* ATCC 55614. These results are also presented graphically in FIG. 4B. The y-axis in FIG. 4B shows the weight of healthy fruit (in grams) at each of three harvests (1, 2 and 3) indicated on the x-axis.

TABLE 7

Weight Healthy Fruit After 7 Days Storage (4° C., 95% RH)

| Treatment | HARVEST 1 Mean ± S.E. | HARVEST 2 Mean ± S.E. | HARVEST 3 Mean ± S.E. |
|---|---|---|---|
| PDB | 140.15 ± 7.16 | 89.97 ± 15.14 | 332.15 ± 53.97 |
| Bacillus | 150.43 ± 22.59 | 192.69 ± 17.26 | 280.73 ± 34.28 |
| Control | 159.49 ± 20.06 | 69.51 ± 7.10 | 239.75 ± 45.00 |
| Rovral | 186.81 ± 12.48 | 120.24 ± 25.85 | 251.56 ± 36.17 |

At the first harvest, no significant differences in healthy fruit weight were observed among the different treatments.

At the second harvest, control and PDB treatments yielded significantly lower healthy fruit weights than the Bacillus treatment, with the Rovral treatment producing significantly lower weight fruit than the Bacillus treatment. At the third harvest, no significant differences were observed among the 4 treatments.

Taken together, the above results indicate that Bacillus ATCC 55614 treatments were as effective as Rovral in controlling losses due to gray mold (% total harvest that is diseased fruit) for the first 2 of 3 harvests.

With regard to healthy fruit, the Bacillus treatments did not result in significantly lower yields than control or PDB treatments, and Bacillus treatments were not significantly less effective than Rovral treatments.

EXAMPLE 8

Fungicidal Activity of ATCC 55614 Culture

To determine if ATCC 556143 was effective against the fungi *Phytophthora infestans, Pythium ultimum, Botrytis cinerea, Rhizoctonia solani*, and *Alternaria solani*, the following experiments were performed. Petri plates were filled with an agar medium (PDA-potato dextrose agar, Difco). Cultures of the above fungi were grown for three days in liquid YPG-1 medium (0.4% yeast extract, 0.1% $KH_2PO_4$, 0.05% $MgSO_4 \cdot 7H_2O$, 1.5% glucose). 0.1–0.2 mL aliquots of spore suspension (concentration approximately $2 \times 10^6$ spores/mL) of pathogen were spread onto the agar. ATCC 55614 was grown in potato dextrose broth (PDB) (Difco) for three days. To test whole broth cultures, the strain was grown to approximately $1 \times 10^6$ to $6 \times 10^6$ CFU/mL and aliquots were taken from these cultures. Supernatant was obtained by density centrifugation of the culture at 5,200 rpm for 20 minutes.

Two 7 mm holes were made in each petri dish. A volume of 100 μL of test sample (either supernatant or whole broth) was added to each 7 mm hole. Each test was performed in duplicate. No microorganism test sample was added to a control plate. The zone of inhibition, measured in millimeters around each hole was measured after 3 to 10 days. Results for Phytophthora, Botrytis, Rhizoctonia, Alternaria and Pythium are shown in Table 8. Control plates showed no zone of inhibition.

TABLE 8

| | Phytophthora | Pythium | Botrytis | Rhizoctonia | Alternaria |
|---|---|---|---|---|---|
| Supernatant | 15 mm | 17 mm | 16 mm | 26 mm | 25 mm |
| Whole broth | 13 mm | 18 mm | 16 mm | Not done | 26 mm |

The same experiment above was performed using a different medium (dextrose, bactopeptone, yeast extract, malt extract) and including the gram-negative bacterium *Pseudomonas syringae*, an important plant pathogen. The results are shown in Table 9.

TABLE 9

| | Phytophthora | Pythium | Botrytis | Rhizoctonia | Alternaria | Pseudomonas |
|---|---|---|---|---|---|---|
| Supernatant | Not done | No zone | Not done | No zone | No zone | 8 mm |

The same experiment was repeated to test ATCC 55614 against the flingus *Trichoderma hayzianuin*, an important pathogen of mushrooms. *Trichoderma harzianum*, strain T-14, was obtained from Campbell. (Davis, Calif.). A number four cork borer was used to make four wells in PDA plates. ATCC 55614 was applied to one of the four wells. Two discs of number four cork borer-sized Trichoderma mycelial plugs were added to each plate in between two wells on each side of the plate. Results were recorded 24 hours later. The size of the cleared zone between the bacterium and the mycelium was recorded. ATCC 55614 produced a 4 mm zone.

To deter-mine in vitro effectiveness of ATCC 55614 against the gram-negative bacterium, *Erwinia herbicola*, and the fuingus, *Monilinia fructicola*, the following experiment was conducted. Bacterial strains were cultured as described above. *Monilinia fructicola* cultures were grown on V-8 agar (20 g agar, 4 g $CaCO_3$, 200 mL V-8 juice) in the dark at room temperature for 8 days. Spores were harvested by placing sterile distilled water on the surface of the culture plates and scraping the surface with a sterile needle to dislodge the spores. Spore concentration was adjusted to $3.3 \times 10^6$ spores/mL and 400 μl added to 4 mL of soft potato dextrose agar. This mixture was poured over the surface of potato dextrose agar culture places and the soft agar allowed to solidify. *Erwinia herbicola* was fermented overnight in half-strength TSA and $1 \times 10^5$ cells were spread on a TSA agar plate. Using a sterile no. 4 cork borer, 5 wells were made in each plate and 100 μl of a three day old culture of ATCC 55614 was added to each well. Plates were incubated at room temperature in the dark and the zones of no growth of the around each well measured. Results are summarized in Table 10.

TABLE 10

Bacterial inhibition of *M. fructicola* and *E. herbicola*

| | *M. fructicola* | *E. herbicola* |
|---|---|---|
| ATCC 55614 | 22 mm | Rep 1 = 23 mm<br>Rep 2 = 27 mm |

EXAMPLE 9

Fungicidal Activity of ATCC 55614 Using Whole Plants

The ability of ATCC 55614 to control late blight (*P. infestans*) infection was tested on whole tomato plants. Tomato plants (Ace and Patio varieties) were purchased from Ace hardware and transplanted into 6 packs having three plants per pack. ATCC 55614 was grown in Trypticase Soy Broth (TSB) (Difco) for 72 hours and reached a concentration of $5 \times 10^6$ CFU/mL. One plant of each variety of tomato plant was sprayed to runoff with a whole broth culture or supernatant of ATCC 55614 and then air-dried at approximately 21° C. Two control plants were untreated. All plants were then sprayed to runoff with a *P. infestans* culture at $1.55 \times 10^5$ CFU/mL. The plants were air-dried at 21° C., lightly misted with deionized water, enclosed in a clear plastic bag and incubated at approximately 16° C. The amount of late blight infestation was recorded fifteen days after treatment. Results are shown in Table 11.

TABLE 11

Light blight and bacterial speck infection fifteen days after treatment with ATCC 55614

| Bacterial strain - Tomato Plant Ace (A) Patio (P) | Whole Broth or Supernatant | # infected leaves/# of total leaves | Percent Infection | Bacterial Speck Infection |
|---|---|---|---|---|
| ATCC 55614(A) | supernatant | 4/34 | 11.7 | No bacterial speck |
| ATCC 55614(P) | supernatant | 3/32 | 9.4 | |
| Average | | | 10.6 | |
| ATCC 55614(A) | whole broth | 7/37 | 18.9 | |

TABLE 11-continued

Light blight and bacterial speck infection fifteen days after treatment with ATCC 55614

| Bacterial strain - Tomato Plant Ace (A) Patio (P) | Whole Broth or Supernatant | # infected leaves/# of total leaves | Percent Infection | Bacterial Speck Infection |
|---|---|---|---|---|
| ATCC 55614(P) | whole broth | 3/25 | 12.0 | |
| Average | | | 15.5 | |
| Phytophthora untreated control | | | | |
| (A) | | 6/26 | 23.1 | 100% covered with speck Full of bacterial speck |
| (P) | | 4/32 | 12.5 | Full of bacterial speck |
| Average | | | 17.8 | |

These results show that the antibiotic-producing strain within the present invention is effective against late blight and bacterial speck.

EXAMPLE 10

Fungicidal Activity of ATCC 55614 Supernatant against *B. cinerea*

To test the effectiveness of the supernatant of bacterial strain ATCC 55614 of the present invention against *B. cinerea*, fresh strawberries picked the day of testing were utilized. For test #1, frozen supernatant of ATCC 55614 was used. ATCC 55614 was grown in potato dextrose broth as previously described. The supernatants were frozen for 1 to 1.5 months before testing. In test #2, ATCC 55614 was grown in either half-strength TSB or in potato dextrose broth (PDB) and the broth or supernatant tested without freezing. Whole broth cultures and supernatants were sprayed onto the strawberries until runoff, then allowed to air dry.

*B. cinerea* spores were grown on potato dextrose agar in a petri plate and scraped into de-ionized water to form a liquid inoculum. The *B. cinerea* inoculum, measuring approximately $5.8 \times 10^5$ cells per mL was sprayed onto the berries until runoff, and the berries allowed to air dry. In test #1, the berries were placed inside a cardboard container with plastic wrap lid at 25° C. In test #2, all berries were place uncovered in an incubator at approximately 16° C. Results are shown in Table 12.

TABLE 12

| Botrytis test Bacterial strain | No. Strawberries per treatment | # infected/# clean |
|---|---|---|
| Test #1 | | |
| ATCC 55614 frozen supernatant | 3 | 0/3 |
| Untreated Control | 3 | 3/0 |
| Test #2 | | |
| ATCC 55614 (PDB) whole broth | 2 | 0/2 |

TABLE 12-continued

| Botrytis test Bacterial strain | No. Strawberries per treatment | # infected/# clean |
|---|---|---|
| ATCC 55614 (PDB) supernatant | 2 | 0/2 |
| ATCC 55614 (TSB) whole broth | 2 | 0/2 |
| ATCC 55614 (TSB) supernatant | 2 | 1/2 |
| Untreated control | 2 | 1/1 |

ATCC 55614 frozen supernatant was completely effective at inhibiting *B. cinerea* infection on live strawberry plants. In addition, the whole broth culture of ATCC 55614 was completely effective at preventing *B. cinerea* infection, regardless of the medium used. Supernatant from ATCC 55614 grown in TSB was partially effective but when grown in PDB, was 100% effective against *B. cinerea*.

EXAMPLE 11

Activity of ATCC 55614 Against Fungal Pathogens

To test ATCC 55614 against a number of fungal pathogens, the strain was grown in potato dextrose broth. Cells were cultured to $5 \times 10^6$ cells/mL. Replicates of three test plants and three control plants per pathogen were utilized. The test plants were each sprayed with a whole broth culture of ATCC 55614 to run-off with a hand-held sprayer. When the foliage had dried, each test plant was sprayed a second time. After the second application of the bacterial strain culture had dried, the test plants and the control plants were inoculated with the appropriate fungal pathogen. Plants were incubated under conditions conducive to disease development. In addition, positive controls were utilized by testing known pesticides against appropriate fungal pathogens in the same manner as the culture of the bacterial strain was tested. Each plant was evaluated by estimating the percent disease control using a scale from 0% control to 100% control. (0=disease level of untreated control; 100=plants with no visible lesions). The final pathogens, resulting diseases, host plant and control pesticides are presented in Table 13. The results are shown in Table 14.

TABLE 13

| Disease | Pathogen | Host Plant | Standard Pesticide |
|---|---|---|---|
| Late Blight | *Phytophthora infestans* | tomato | metalaxyl |
| Early Blight | *Alternaria solani* | tomato | propiconazole |
| Oray Mold | *Botrytis cinerea* | pepper | propiconazole |
| Downy Mildew | *Plasmopara viticola* | grape | metalaxyl |
| Powdery Mildew | *Uncinula necator* | grape | propiconazole |
| Leaf Rust | *Puccinia recondita* f.sp. *tritici* | wheat | propiconazole |
| Glume Blotch | *Staganospora nodorum* | wheat | propiconazole |

TABLE 14

| Treatment | Rate (ppm) | Pi[y] | As | Pv | Un | Bc | Sn | Pr |
|---|---|---|---|---|---|---|---|---|
| ATCC 55614 | — | 7 | 0 | 100 | 0 | 100 | 0 | 73 |
| metalaxyl | 30 | 90 | — | 100 | — | — | — | — |

TABLE 14-continued

| Treatment | Rate (ppm) | Pi[y] | As | Pv | Un | Bc | Sn | Pr |
|---|---|---|---|---|---|---|---|---|
| | 20 | — | — | 67 | — | — | — | — |
| | 10 | 47 | — | — | — | — | — | — |
| myclobutanil | 10 | — | — | — | 100 | — | — | — |
| | 1 | — | — | — | 0 | — | — | — |
| propiconazole | 250 | — | 93 | — | — | — | — | — |
| | 30 | — | 37 | — | — | — | — | — |
| | 10 | — | — | — | — | 100 | 100 | — |
| | 5 | — | — | — | — | 63 | 73 | 95 |
| | 1 | — | — | — | — | — | — | 33 |
| Disease Index (%)[z] | — | 50 | 80 | 75 | 30 | 80 | 80 | 80 |

[y]Pi = *P. infestans*, As = *A. solani*, Pv = *P. viticola*, Un = *U. necator*, Bc = *B. cinerea*, Sn = *S. nodorum*, Pr = *P. recondita* f.sp. *tritici*.
(%)[z] Disease index = percent diseased tissue on the untreated, inoculated plants.

ATCC 55614 provided complete control of *B. cinerea*. ATCC 55614 was also highly active against grape downy mildew and leaf rust, and had slight activity against Phytophthora in this test.

EXAMPLE 12

Activity of ATCC 55614 against brown rot, *Monilinia fructicola*

A 250 mL culture of ATCC 55614 was grown for 3.5 days in PDB as previously described. Peaches were purchased from a local grocery store (Safeway) and were surface sterilized with a 10% Clorox solution, rinsed with deionized water and air dried. Whole fermentation broths of ATCC 55614 ($8.7 \times 10^6$ CFU/mL) were sprayed with a hand-held sprayer on two peaches until runoff (approximately 50 mL per two peaches). The peaches were allowed to air dry. Monilinia spores were scraped from a petri plate and suspended in deionized water to a concentration of $1.09 \times 10^5$ spores/niL. The peaches were then sprayed with the spore suspension until runoff and allowed to air dry. Two peaches were untreated and two peaches were sprayed with Monilinia only. The peaches were placed in a polypropylene container in an incubator in the dark at 18° C. for four or six days. The amount of brown rot on each peach was measured, as show in Table 15.

TABLE 15

ATCC 55614 Inhibition of Monilinia in Peaches

| | Size of Monilinia Lesion after 4 days | Size of Monilinia Lesion after 6 days |
|---|---|---|
| ATCC 55614 treated #1 | 1.5 × 1 cm | 5 × 5 cm |
| ATCC 55614 treated #2 | No infection | No infection |
| Untreated #1 | 9 × 7 cm | 11 × 7 cm |
| Untreated #2 | 3 × 2 cm | 11 × 12 cm |
| Monilinia treated #1 | 7 × 5 cm | 10 × 10 cm |
| Monilinia treated #2 | 4 × 3 cm | 10 × 6 cm |

At both four and six days, ATCC 55614 suppressed Monilinia brown rot compared to the untreated controls and Monilinia only peaches. After six days, the control peaches were all heavily infected with brown rot, while only one of the ATCC 55614 peaches showed infection. Furthermore, the one infected ATCC 55614 peach had a lesion which was much smaller than those in the untreated or Monilinia only controls.

Comparison of ATCC 55614 and Chemical Fungicide Inhibition of *Monilinia fructicola*

Using the same protocol as described above to grow ATCC 55614 cultures and Monilinia spores, the effect of ATCC 55614 was compared to the commercially available fungicide Benlate® (benomyl). Results are shown in Table 16.

TABLE 16

ATCC 55614 and Benlate ® Inhibition of Monilinia in Peaches

|  | Size of Monilinia Lesion after 4 days | Size of Monilinia Lesion after 6 days |
| --- | --- | --- |
| ATCC 55614 treated #1 | 1.5 × 1.0 cm | 3 × 4 cm |
| ATCC 55614 treated #2 | No infection | No infection |
| Benlate ® treated #1 | 1.25 cm × 1.0 cm | 3 × 3 cm |
| Benlate ® treated #2 | No infection | No infection |
| Monilinia treated #1 | 3.5 × 3.5 cm | 5 × 7 cm |
| Monilinia treated #2 | No infection | No infection |

These results show that ATCC 55614 is as effective in controlling Monilinia infection as the commercial fungicide, Benlate ®.

These results show that ATCC 55614 is as effective in controlling Monilinia infection as the commercial fungicide, Benlate®.

While the invention has been described with reference to specific methods and embodiments, it will be appreciated that various modifications and changes may be made without departing from the invention.

What is claimed is:

1. A method for producing a *B. subtilis* composition having antimicrobial activity which comprises culturing in a culture medium *B. subtilis* strain ATCC 55614.

2. A method for isolating a bioactive extract produced by *B. subtilis* strain ATCC 55614 which comprises culturing in a culture medium *B. subtilis* strain ATCC 55614 and isolating from the culture medium the bioactive extract produced by the *B. subtilis* strain.

3. A method for isolating a bioactive extract produced by *B. subtilis* strain ATCC 55614 which comprises:

(i) culturing in a culture medium *B. subtilis* strian ATCC 55614;

(ii) extracting a bioactive component present in the cell culture medium to produce a crude extract;

(iii) separating the crude extract on a solid support to produce separated fractions; and (iv) screening the separated fractions from antimicrobial activity.

4. The method of claim 3, further comprising the step of:

(v) pooling the active fractions identified in step (iv).

* * * * *

UNITED STATES PATENT AND TRADEMARK OFFICE
CERTIFICATE OF CORRECTION

PATENT NO : 6,004,774
DATED : 21 December 1999
INVENTOR(S): Pamela G. Marrone, et al.

It is certified that error appears in the above-identified patent and that said Letters Patent are hereby corrected as shown below:

In the Other Publications Section, column 2, line 43, "*subtilisas*" should be --*subtilias*--.

In the Abstract, line 4, "fingal" should be --fungal--.

At column 1, line 67, "Veriag" should be --Verlag--.

At column 2, line 33, after *Fragaria*, delete "'"; line 51, "fingistats" should be --fungistats--; and "fingal" should be --fungal--.

At column 3, line 1, "ph.topathogenic" should be --phytopathogenic--; and line 64, "usefuil" should be --useful--.

At column 4, line 2, "fildly" should be --fully--; line 28, "MYcosTOP" should be --MYCOSTOP--; line 53, "Supematant" should be --Supernatant--; line 56, "defmed" should be --defined--.

At column 5, line 2, "fingi" should be --fungi--; line 35, "Fruit-bearng" should be --Fruit-bearing--.

At column 6, line 35, "cinera" should be --cinerea--; line 67, "flimgal" should be --fungal--.

At column 7, line 1, "fuingal" should be --fungal--; line 2, "flungi" should be --fungi--; line 3, "flingal" should be --fungal--; line 11, "fuingal" should be --fungal--; line 16, "chraracterized" should be --characterized--; line 21, "subtills" should be --subtilis--; line 32, "usefid" should be --useful--; line 35, "Scaaad" should be --Schaad--.

UNITED STATES PATENT AND TRADEMARK OFFICE
CERTIFICATE OF CORRECTION

PATENT NO : 6,004,774
DATED : 21 December 1999
INVENTOR(S): Pamela G. Marrone, et al.

It is certified that error appears in the above-identified patent and that said Letters Patent are hereby corrected as shown below:

At column 8, line 7, "scierotia" should be --sclerotia--; line 20, "denorinator" should be --denominator--; line 63, "fuither" should be --further--.

At column 9, line 14, "other. materials" should be --other materials--; line 60, "aqueous, flowable" should be --aqueous flowable--.

At column 10, line 1, "formation" should be --formulation--; line 22, "garnma" should be --gamma--; line 29, "bofiran" should be --bofuran--; line 35, "diphenylguaaidine" should be --diphenylguanidine--.

At column 11, line 10, "chirneric" should be --chimeric--.

At column 13, line 29, "11" should be --1L--; line 41, "mm ' 15" should be --mm x 15--; line 69, "gro.Nh" should be --growth--.

At column 14, line 21, "fuingal" should be --fungal--.

At column 14, line 34, after the Table 1, add
--[1]a. Growth assayed 7 days after inoculation with a 5 mm mycelial plug.
  b. Growth conditions = 200C, 16-hour day period.
  c. Mean and SD calculated for n = 10
[2]Means are significantly different than control (alpha = 0.01), Dunnett Test.--

At column 15, line 49, after "0.01)", add --, Dunnett Test--.

UNITED STATES PATENT AND TRADEMARK OFFICE
CERTIFICATE OF CORRECTION

PATENT NO. : 6,004,774
DATED : 21 December 1999
INVENTOR(S) : Pamela G. Marrone, et al.

It is certified that error appears in the above-identified patent and that said Letters Patent is hereby corrected as shown below:

At column 15, line 62, "scierotia" should be --sclerotia--.

At column 16, line 16, "1.0 ' $10^5$" should be --1.0 × $10^5$--; line 19, "250°" should be --25°--.

At column 17, line 13, "cells/nil" should be --cells/mL--.

At column 18, line 9, "tirne" should be --Time--.

At column 20, line 56, " flingus *Trichoderma hayzianuin*" should be --fungus *Trichoderma harzianum*--; line 66, "determine" should be --determine--.

At column 21, line 1, "fuingus" should be --fungus--.

At column 23, line 53, "oray" should be --Gray--.

At column 24, line 40, "/niL" should be --/mL--.

At column 26, line 22, "from" should be --for--.

Signed and Sealed this

Twenty-fourth Day of April, 2001

Attest:

NICHOLAS P. GODICI

Attesting Officer

Acting Director of the United States Patent and Trademark Office